United States Patent [19]
> Tamari et al.

[11] Patent Number: 5,013,303
[45] Date of Patent: May 7, 1991

[54] CONSTANT PRESSURE INFUSION DEVICE

[76] Inventors: Yehuda Tamari, 12 Pondview Dr., Muttontown, N.Y. 11791; Michael B. Meyers, 1 Willow Rd., Woodbury, N.Y. 11797

[21] Appl. No.: 267,235

[22] Filed: Nov. 3, 1988

[51] Int. Cl.$^5$ ............................................ A61M 37/00
[52] U.S. Cl. ............................ 604/140; 128/DIG. 12; 604/131
[58] Field of Search ............................... 604/131–132, 604/134–135, 140–143, 147; 222/95, 386.5; 128/DIG. 12

[56] References Cited

U.S. PATENT DOCUMENTS

| | | | |
|---|---|---|---|
| 2,618,977 | 2/1953 | Hottenroth | 73/715 |
| 2,842,123 | 5/1958 | Rundhaug | 604/141 |
| 3,044,663 | 7/1962 | Norton et al. | 604/141 |
| 3,468,308 | 6/1969 | Bierman | 604/141 |
| 3,478,695 | 2/1968 | Goranson et al. | 417/379 |
| 3,506,005 | 3/1970 | Gilio et al. | 604/132 |
| 3,572,979 | 3/1971 | Morton | 417/390 |
| 3,902,635 | 9/1975 | Jinotti | 222/103 |
| 3,993,069 | 11/1976 | Buckles et al. | 604/132 |
| 4,048,994 | 9/1977 | Lo | 604/142 |
| 4,090,514 | 5/1978 | Hinck | 604/142 |
| 4,201,207 | 5/1980 | Buckles et al. | 604/132 |
| 4,203,441 | 5/1980 | Theeuwes | 604/892.1 |
| 4,300,543 | 11/1981 | Baron | 128/90 |
| 4,337,769 | 7/1982 | Olson | 604/251 |
| 4,379,453 | 4/1983 | Baron | 604/145 |
| 4,419,096 | 12/1983 | Leeper et al. | 604/132 |
| 4,430,078 | 2/1984 | Srague | 604/141 |
| 4,507,116 | 3/1985 | Leibinsohn | 604/142 |
| 4,539,005 | 9/1985 | Greenblat | 222/95 |
| 4,551,136 | 11/1985 | Mandl | 604/141 |
| 4,673,392 | 6/1987 | Keime | 128/DIG. 12 |
| 4,722,732 | 2/1988 | Martin | 604/132 |
| 4,735,613 | 4/1988 | Ballin et al. | 604/141 |

OTHER PUBLICATIONS

Rephael Mohr et al., "Biocoff-A New Pressure Device for Infusion Bags", *Critical Care Medicine*, vol. 13, No. 12, 1985, pp. 1050-1051.
Electromedic Incorporated–Advertisement.
Biomedical Dynamics–Advertisement.
Curtin Matheson–Advertisement.
Medex Incorporated–Advertisement.
Bay Medical–Advertisement.
Alton Dean Medical–Advertisement.
Extracorporeal Sa.–Advertisement.
Shiley–Advertisement.

Primary Examiner—Stephen C. Pellegrino
Assistant Examiner—Michael Rafa
Attorney, Agent, or Firm—Scully, Scott, Murphy & Presser

[57] ABSTRACT

The specification discloses a disposable low-cost constant pressure infusion pump intended to be used with an infusion cuff, or other infusion device for the infusion of sterile physiological solutions into the human body. The device utilizes an enclosure, which may be an infusion cuff or a pressurizing chamber that is adapted to receive a disposable bag of physiological solutions therewithin. A pressurizing chamber is formed about and around the bag of physiological solution, to define a pressure chamber to which is supplied a regulated pressure. The regulated pressure is provided from a small low-cost disposable canister of freon or other pressurizing fluid through a pressure regulating mechanism. The canister is equipped with a springloaded discharge valve, and the pressure regulating mechanism balances the spring constant of this discharge valve against an elastic wall or other resilient diaphragm to balance the loading between the elastic wall and spring-loaded discharge valve. A variety of actuating means and mechanisms are disclosed for balancing the two force specters to achieve a predetermined regulated pressure.

23 Claims, 7 Drawing Sheets

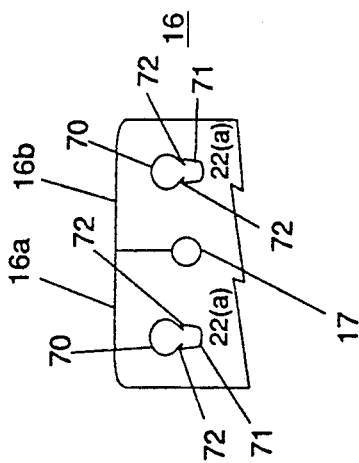
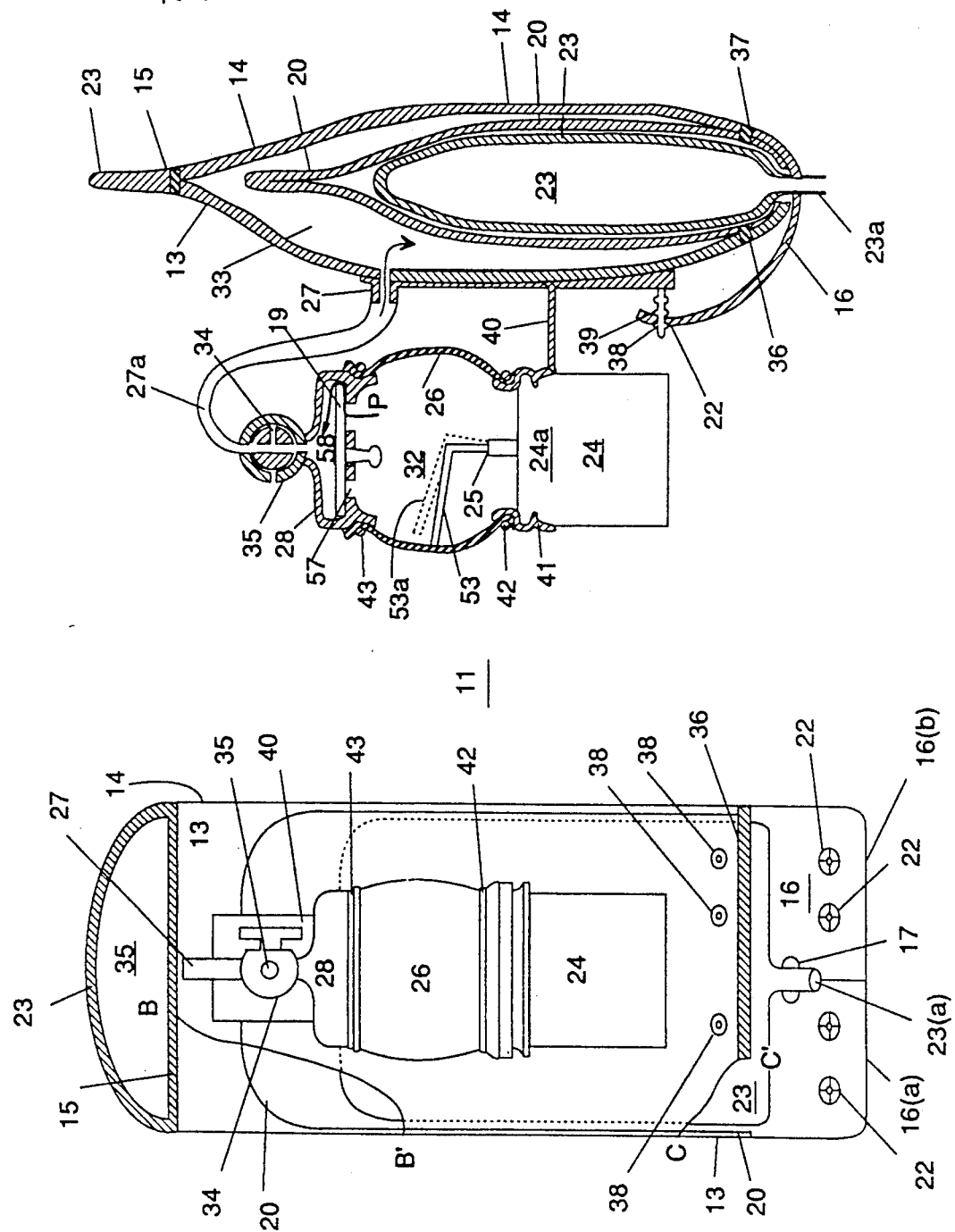

FIG. 17
FIG. 18
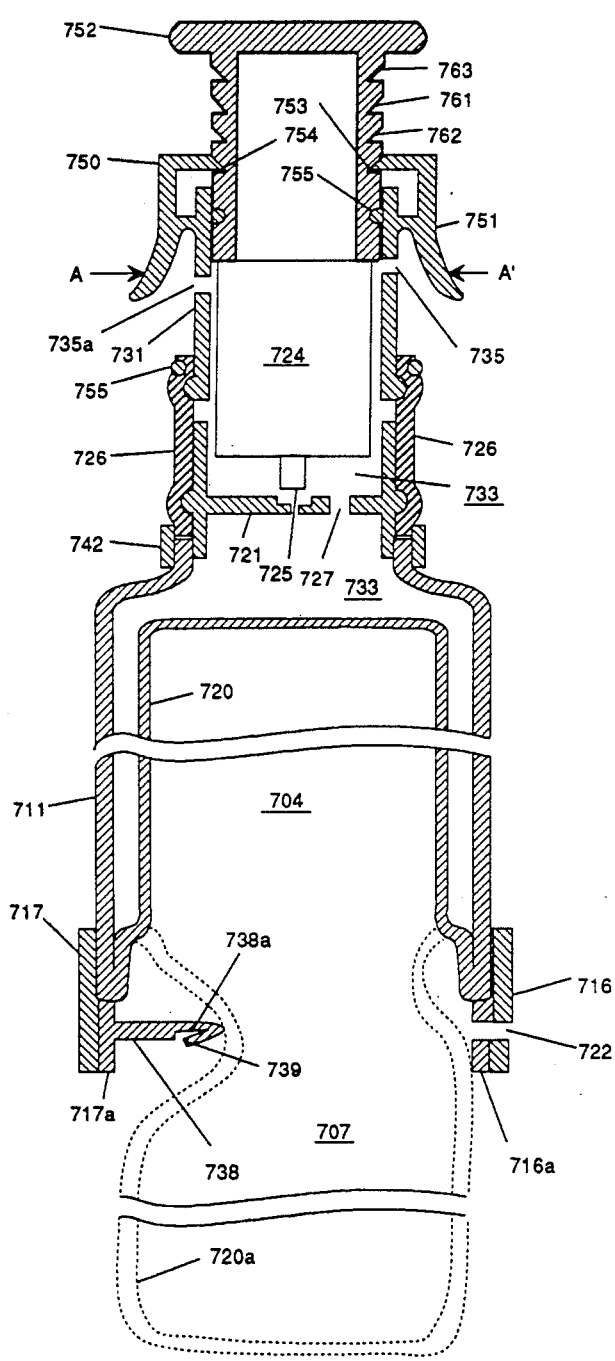
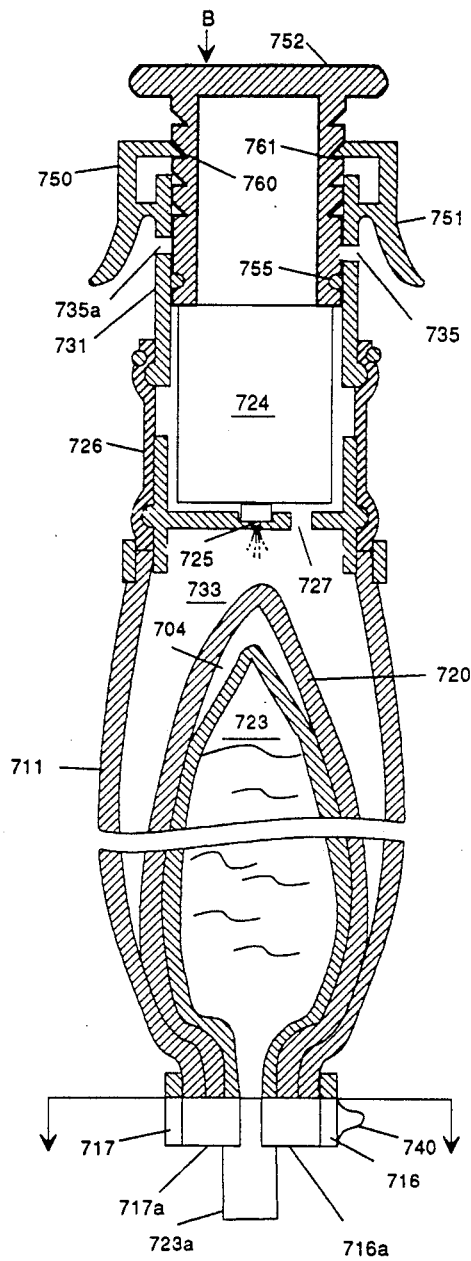
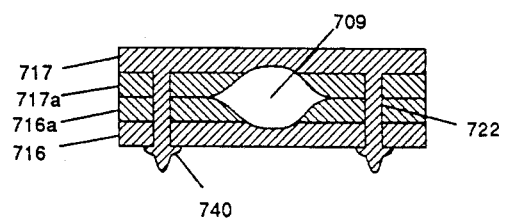
FIG. 20

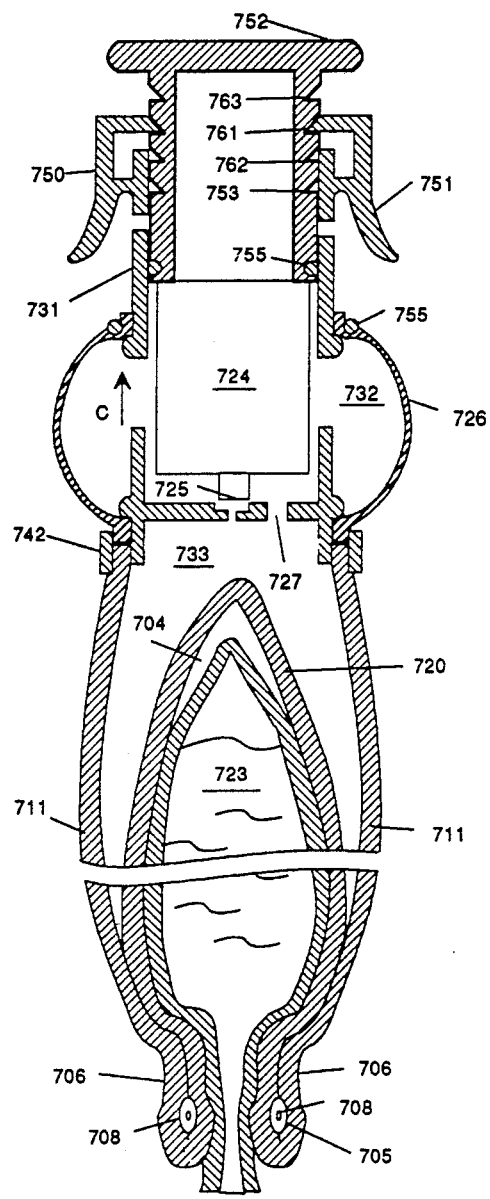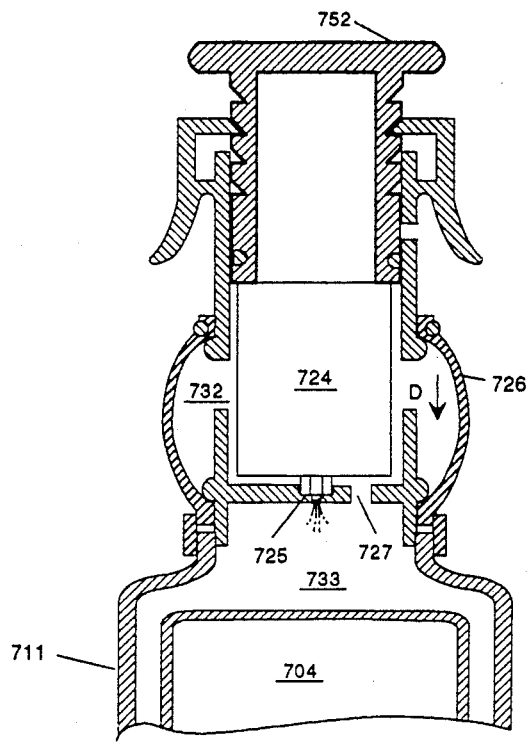
FIG. 19a
FIG. 19

CONSTANT PRESSURE INFUSION DEVICE

FIELD OF THE INVENTION

The present invention is a disposable low cost constant pressure infusion pump to be used for the infusion of physiological solutions into a patient receiving medical care. It is useful not only for hospitals, but also for medical field units, such as ambulances, Red Cross teams or battle field medics.

BACKGROUND OF THE INVENTION

Physiological solutions stored in plastic bags need to be pressurized when infusion of the solutions is inhibited by either high solution viscosity (e.g., pack red blood cells), high pressure (e.g., infusion into the arterial tree), or when rapid infusion is required (e.g. crystalloid cardioplegia, hypovolumic shock). In addition, flush solutions used during invasive pressure measurements need to be pressurized to a constant pressure in order to maintain a constant infusion to keep the intravascular catheter patent. There are presently several types of devices that are commercially available to pressurize bags. The most popular is a two compartment soft bag with an inflatable bladder on one side and a pocket on the other side. The bag to be pressurized is inserted in the pocket. The bladder is inflated with air via a hand pump, tubing and valves. As the bladder inflates, it imparts external compression on the encased bag in the pocket. A pressure gauge indicates the pressure within the bladder. This type of device is illustrated in U.S. Pat. No. 4,090,514.

A second type of device available is a non-disposable rigid housing into which the solution bag is inserted. The bag is compressed by a spring-loaded plate which also supports the bag within the housing. The spring-loading is engaged by a mechanical crank mounted on the box. This type of device is illustrated in U.S. Pat. No. 3,902,635. A third type of device is similar to the first two types except that it incorporates a pressure regulator that maintains the inflatable bladder at a constant pressure. The unit requires an external gas source (e.g. "wall-supplied" oxygen) and is very expensive.

These commercially available devices have the following problems:

1. Cost - All, except one, are non-disposable, and relatively expensive. A variety of non-repairable malfunctions make the life expectancy of these devices short.

2. Sterility - They are used with blood, blood products and intravenous solutions in high risk areas of the hospital where cross contamination between patients is a prime consideration. Washing and/or sterilization of the non-disposable units is not easy and can lead to failure of these units.

3. Accuracy - Inaccurate infusion pressure occurs as the physiological solution is infused. The soft system, intermittently has to be manually compressed to maintain the same compression pressure against the bag with the physiological solution. Even when the compression pressure is maintained constant, the infusion pressure decreases as the volume in the bag decreases. Therefore, proper bladder pressure, as indicated on the pressure gauges, does not assure proper infusion pressure. The prior art systems require appropriate initial over pressurization, higher than 400 mmHg, to maintain the infusion pressure above 250 mmHg, as the volume of the bag changes from full to empty. When the bag's volume is emptied to 100 ml, the pressure may be as low as 200 mmHg. Additional inaccuracies may occur with (a) inappropriate placement of the bag within the compression devices causing herniation and solution trapping, a decrease in infusion pressure and decrease in infusion rate; (b) malfunctioning gauges - the gauges are usually not calibrated and are usually discarded only if "stuck". In fact the manufacturer of one of the most widely used pressure cuffs warns against the use of the cuff for use in monitoring arterial or venous pressure.

4. Safety - A decrease in infusion rate can be detrimental to the patient in two ways. First, the patient does not get the required solutions at the rate set initially unless an adjustment is made in the flow controlling resistor located in the I.V. line. Second, when heparinized solutions are used for continuous flush of intravascular catheters, a decrease in flush solution can result in formation of thrombus at the catheter tip which may lead to vessel damage and inaccurate pressure reading. The latter can result in an inappropriate therapy. The rigid device also poses a possible safety hazard to a patient lying under it. Should the device fall, patient injury can result.

In addition to the devices that are currently commercially available, the prior art includes a number of patents which describe constant pressure infusion pumps which include both ambulatory devices, and fixed location devices intended to be attached to hospital air supplies.

U.S. Pat. No. 3,468,308 discloses a pressure infusion device for ambulatory patients with a pressure control means. FIGS. 10-12 of this reference disclose an infusion device having a portable $CO_2$ cartridge, a separate pressure regulator, a pressure chamber, and a bladder for discharging a solution into an ambulatory patient This device, however, is not intended to be a low cost disposable device which may be disposed of to avoid cross-contamination of patients. In addition, it is not capable of receiving standard disposable bags of physiological solution. The saline bladder must be refilled after each discharge.

U.S. Pat. No. 2,842,123 and 3,044,663, disclose pressurized transfusion devices that are particularly adapted to be connected to a compressed air line available in most hospitals. These devices are not disposable low cost devices, nor are they capable of accepting or discharging the contents of disposable bags of physiological solution.

U.S. Pat. No. 4,048,994 describes a self inflating liquid container for physiological solutions that may be disposed of. The devices are adapted to be pressurized by a sealed cartridge of $CO_2$, but it is not a constant pressure device, nor may it be reused with disposable bags of sterile physiological solutions.

U.S. Pat. No. 4,507,116 discloses a device particularly adapted for receiving and discharging the contents of a disposable bag of sterile physiological solutions. The device includes an accumulator 20 which is intended to be dilated with excess pressure pumped by bulb 10 to maintain the discharge pressure of the device at a somewhat constant level. The device uses a relatively linear portion along the curve of elastic deformation of the bladder to provide its constant discharge pressure. While conceptually feasible, the device would require an accumulator having the capacity to store, at the desired pressure-volume ratios, the amount of air necessary to discharge 500 to 1000 ml of solution, before a constant pressure could be achieved for the entire bag of solution. This would result in a rather bulky and expensive device with the volume of the accumulator approaching that of the infusion device.

U.S. Pat. Nos. 3,506,005 and 4,419,096 disclose constant pressure infusion devices, wherein the constant pressure is supplied by elastomatic bladders that are expanded along a linear portion of their curves of elastic deformation to achieve their constant pressure discharge.

U.S. Pat. No. 4,379,543 discloses an infusion device particularly adapted for use with disposable bags of sterile physiological solution, wherein the pressure generating means for discharging this solution is supplied by a pair of chemical agents which generate a gas when mixed. However, once activated, the device generates a fixed amount of compressed gas, and the discharge of the physiological solution for the bag results in a declining pressure for the discharge solution. The device does not utilize any pressure regulating means. Similar gas generating devices intended for use in the medical field are also disclosed in U.S. Pat. Nos. 4,203,441 and 4,300,542.

Since the currently available prior art devices are expensive, and not disposable or if disposable, are inacurate and possibly dangerous to the patient, it is felt that a device which would overcome these problems would be both new and useful.

OBJECT OF THE INVENTION

It is therefore an object of the present invention to provide a disposable device having a self inflation feature that would receive one or more disposable bags of physiological solution, and provide a constant infusion pressure for the physiological solutions when they are discharged from the disposable bags.

The present invention pressurizes a disposable bag with a preassembled disposable device that provides accurate infusion pressure, safety, cleanliness, and is simple and fast to set up and use. The device incorporates a constant pressure means by which the bag is pressurized to a constant pressure, usually 300 mmHg.

To obtain constant infusion pressure, the disposable bag must be compressed by constant pressure along a relatively uniform surface area and be supported on its other sides to prevent herniation.

A self-pressurizing infusion bag may require means to maintain the bag unpressurized during storage, means to pressurize the bag, means to initiate the pressurization, means for maintaining pressure within desired limits, a pressure indicator, and means to relieve over-pressurization. It should be safe, inexpensive, compatible with a medical environment and be simple to operate.

A standard gas filled container, e.g., an aerosol can, can be used to provide a gas source to pressurize the bag. Means must be provided to introduce more gas to compress the disposable solution bag at a constant pressure as the disposable bag is emptied.

The pressurized fluid may be compressed gas and/or a liquid with a boiling point below the expected operating temperature of the device, with its vapor pressure at that temperature much greater than the desired regulated pressure. A liquid, such as chlorofluorocarbon (CFC), requires a significantly lower volume container for the same expanded gas volume as does $CO_2$ and it is therefore preferred. To stay within the EPA regulations only chlorofluorocarbons that are not fully halogenated are to be used. A good choice is the non-flammable 40%/60% blend of CFC 22/142a (a) "Genetron Propellants in Aerosol Products" publication no. TSD-0485 Allied Corp. (b) "A New Era in Aerosol Propellants" publication no. E-70287 DuPont, Inc. For these gases, a neoprene valve stem should be used in the aerosol can.

It is therefore an object of the present invention to provide a low cost, inexpensive and disposable constant pressure infusion pump for dispensing a physiological solution from a sterile disposable bag. The pump includes a housing member having a sealable container with non-expandable walls. The disposable bag is placed within the container, and within or against a flexible wall which is used to pressurize the disposable bag. The pump is provided to receive a canister of pressurized fluid as a pressure source. The canister is equipped with a discharge valve for intermittently dispensing the pressurized fluid and is in fluid communication with the sealable container or an inflatable bladder within the container.

In one embodiment of the invention, a first pressure chamber is adapted to receive the canister of pressurized fluid, and the canister is equipped with a spring-loaded discharge valve which discharges the pressurized fluid into the first pressure chamber when actuated. The first pressure chamber has at least one elastic wall adjacent the spring-loaded valve, which when stressed, generates a contractive force along a force vector. A means is then employed to engage the spring-loaded discharge valve with the contracting force and thereby pressurize the first pressure chamber to a predetermined constant pressure. Variations in the elastic wall thicknesses, configuration and material are used to determine the constant pressure as will be hereinafter explained.

It is also an object of the present invention to provide an inexpensive and low cost constant pressure pump that may be formed from plastic, with the pressure source being an inexpensive canister of liquified gas, such as CFC.

It is further an object of the present invention to provide a pressure regulated gas source that may be used to discharge the contents of a disposable bag filled with sterile physiological solution, whether the bag is placed in a sealed container or in a restraint cuff.

It is further an object of the present invention to provide a reciprocating means that can actuate or be responsive to a wide variety of valves that may be found on pressurized canisters of gas.

It is a further object of the invention to provide a simple inexpensive pressure regulating mechanism responsive to excess pressure in the system to prevent over-pressurization of the physiological solution.

It is another object of the present invention to provide a variety of actuating mechanisms that may be used with a disposable device at the present invention, wherein the device may be stored for long periods of time without danger of discharge of the gas. When initiation of the gas pressure generating mechanism is desired, a simple push, pull, or twist mechanism is employed to initiate pressurization of a bladder surrounding a bag of physiological solution.

It is another object of the present invention to provide a disposable housing and bladder combination to reduce the pressure differential between gas and pressurized liquid that characterizes present devices.

It is another object of the present invention to provide a disposable device that is equally operable in hospitals, or in remote field locations, such as ambulances, Red Cross emergency sites, or war time field hospitals.

BRIEF DESCRIPTION OF THE DRAWINGS

FIG. 1 is a front view of one embodiment of the present invention having a flexible, but non-expandable pressure chamber, with triple break away views to illustrate the inner construction.

FIG. 2 is a cross-section of the device illustrated in FIG. 1, illustrating a disposable bag of physiological solution disposed therein.

FIG. 2(a) is a plan view of an alternative configuration of the closing flap 16 and one way securing means 22.

FIG. 17 is a cross-sectioned and diagrammatic view of still another embodiment of the invention, illustrating the pressure regulator means before actuation.

FIG. 18 is a cross-sectional and diagrammatic partial view of the embodiment illustrated in FIG. 17 after actuation, but before pressure regulation.

FIG. 19 is a cross-sectioned and diagrammatic view of the embodiment illustrated in FIG. 17 illustrating a state of pressure regulation, and an alternate closure means.

FIG. 19a is a cross-sectioned and diagrammatic view of the embodiment illustrated in FIG. 17 illustrating a second state of pressure regulation.

FIG. 20 is a cross-sectioned diagrammatic view of an alternate form of the closure means used on the embodiment illustrated in FIG. 17.

DETAILED DESCRIPTION OF THE PREFERRED EMBODIMENTS

Figures 3, 4, 5:
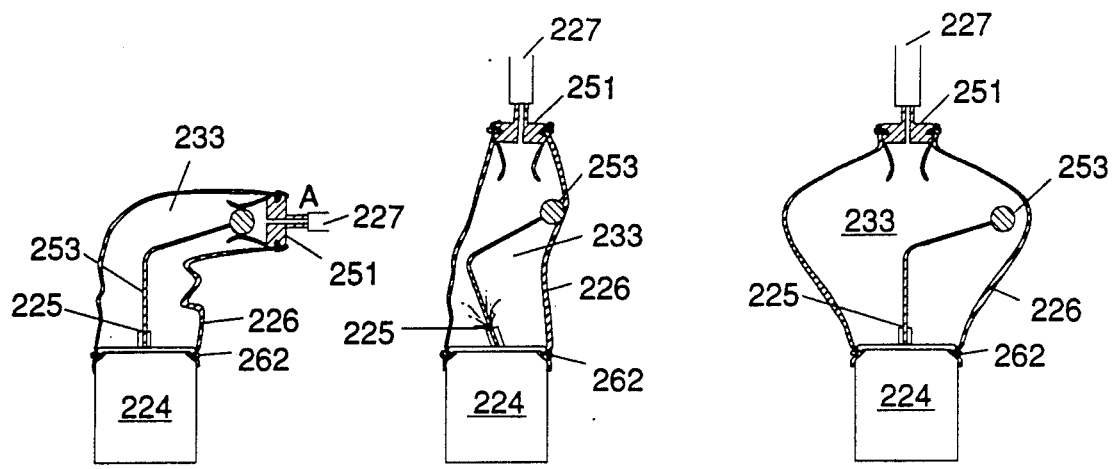
FIG. 3 is a diagrammatic illustration of the second embodiment of the present invention, illustrating the configuration of the device when shipped.
FIG. 4 is a diagrammatic illustration of the second embodiment of the present invention, illustrating the initial actuation and pressurization of the device.
FIG. 5 is a diagrammatic illustration of the second embodiment of the present invention, illustrating the pressurized state.

FIG. 1 is a frontal break away illustration of a first embodiment of the present invention. In this embodiment, a housing member 11 and bladder 20 are formed from inexpensive flexible plastic walls to define a cavity for receiving a disposable bag of sterile physiological solution 23. Sterile physiological solution, as that term is used in this specification includes normal saline, blood, and cardioplegia solutions as representative examples. The cavity is defined by bladder 20 which is surrounded by "layflat" tubing having opposing side walls 13, 14 which are sealed along the top at 15, and along the bottom with double seals 36, 37 and lower flap 16. Flap 16 has a slot 17 defined therein for receiving a conduit which extends from a disposable bag of sterile physiological solution 23. One or more of the housing walls may be formed of a clear or transparent plastic to permit direct observation of the bag to permit observation of the fluid level in the sterile bag during discharge of the physiological solution. The cavity 12 is closed by flap member 16 and latched by means of a plurality of one way latch mechanisms 22 which may be formed within the lower flap 16, the operation of which will be further described with respect to FIG. 2.

In FIG. 2, the device of FIG. 1 is shown in cross-section with the flap member 16 closed, and the sterile bag of physiological solution 23 installed therein. As illustrated in FIG. 2, a bladder means 20 has been pressured to approximately 300 mmHg, and is exerting a constant pressure on the side wall of the disposable bag 23.

In the embodiment illustrated in FIGS. 1 and 2, the front and rear sidewalls 13 and 14 are heat sealed across their upper periphery as indicated at 15 and 23, to provide an opening 35 which may be used to suspend the infusion device from a standard intravenous solution hanger. Likewise, the lower portions of sidewalls 13 and 14 are also sealed, as indicated by seal 36 in FIG. 1 and seals 36, 37 in FIG. 2. However seals 36, 37 do not seal sidewalls 13 and 14 to one another, but rather seal the inner bladder member 20 to the sidewalls to define the first pressure chamber 33 therebetween. Thus, when flap 16 is open as illustrated in FIG. 1, the bag of physiological solution 23 inserted upwardly into the interior of bladder 20, between sidewalls 13 and 14. Since sidewalls 13 and 14 are nonexpandable, when the first pressure chamber 33 is pressurized, the pressure exerted thereon, will be transmitted by bladder 20 to the bag of physiological solution 23.

Bladder 20 may also be formed of soft "lay flat" tubing, including thin wall (0.002 to 0.010 inches) polyethylene, nylon polyester, polyester-polyethylene, polypropelene and the like, and provides a readily conformable bladder which surrounds the bag of physiological solution. By using a soft conformable material, it is possible to obtain a solution pressure that is equal to the cuff pressure. Common fluid cuffs with stiffer side walls result in initial over pressurization, as high as 400 mmHg which then declines as the solution is discharged, to the extent that an air pressurization of 300 mmHg may result in a solution pressurization of only 100 mmHg. In contrast, the soft conformable bladder enables a more efficient transfer of air pressure to solution pressure, which virtually eliminates the initial over pressurization and the decline in solution pressurization found in prior art devices.

Flap member 16 is secured to sidewall 13 by means of a plurality of one way securing devices 22 which are placed as often as necessary across the lower periphery of sidewall 13, and flap 16. Each of the securing means 22 comprises a one way plastic disk formed in flap member 16, and a series of spherical balls illustrated at 38, 39 in FIG. 2. The purpose of the spherical balls is to insure the user of the infusion device does not attempt to reuse the device beyond the capacity of the propellant or CFC gas in canister 24. If it is desired to provide enough gas in canister 24 for three uses of the device, three balls similar to 38 and 39 are formed on the fastener means affixed to sidewall 13. Each time the device is used, the one way portion 22 formed in flap 16 is snapped over the outermost ball until the contents of the bag of physiological solution 23 is exhausted. When the bag is changed, the outer ball 38, illustrated in FIG. 2 is snipped or broken off, and the inner bag replaced. When the inner bag is replaced, the fastening means 22 will snap over the inner ball 39, indicating the last and final use of the disposable infusion device. By keying the number of balls on the fastening means 22 to the amount of propellant gas in canister 24, one can avoid the inadvertent use of the device after the canister 24 is substantially exhausted.

FIG. 2(a) illustrates an alternate form of flap 16 having a different one way fastener 22a. The fastener includes an enlarged portion 70 for receiving the ball 38, and a key way 71 for receiving the connecting portions between balls 38 and 39. The inner walls of key way 22 include one way projections 72 which extend inwardly to prevent the return of balls 38, 39 and the interconnecting portion to the enlarged opening 70. As illustrated in FIG. 1 and 2(a), flap 16 includes a first portion 16a and a second portion 16b with a slit therebetween for quick and easy insertion of outlet tube 23a into the opening 17.

As illustrated in FIG. 2, the canister of CFC propellant 24 is snapped into a plastic frame member 40 which is secured to sidewall 13 by heat sealing, adhesive or the like. Frame member 40 contains a snap ring 41 which receives the upper annular groove 24a formed on the upper outer wall of canister 24. By utilizing a latex lined plastic such as polyethelene the snap ring 41 will be made self-sealing with respect to canister 24, or in the alternative, an adhesive sealant may be used to secure snap ring 41 to canister 24. The elastic sidewall 26 is secured to snap ring 41 by means of a band 42 or by adhesive. Likewise, the elastic wall 26 is secured the upper cap 28 by means of band 43 or by means of a suitable adhesive. Disposed across the upper passageway of end cap 28 is a one way valve means 19 which enables only one way communication between pressure chamber 32, and pressure chamber 33. This is to prevent the possible occurrence of uncontrolled expansion of sidewall 26 in the event the canister is pressurized by the operator above point c of the pressure/volume curve illustrated in FIG. 6. One way valve 19 is a disk of elastic material such as latex or silicone that normally covers a series of openings 27 which provide passageway between pressure chamber 22 and conduit 27. When the pressure in chamber 33 is higher than the pressure in chamber 32, which might occur by an attendant squeezing the outer sidewalls of the infusion device, or from an increase in temperature of this gas. One way valve 19 prevents the transmission of such excess pressure back into chamber 32.

FIG. 1 illustrates the bag with a first break away portion A—A' illustrating the material under the flap 16. A second break away B—B' illustrates the bladder member 20 sandwiched between sidewalls 13 and 14, with the bag of physiological solution illustrated by dotted lines. Break away portion C—C' illustrates the third layer between the bag of physiological solution 23 and the bladder 20.

The pressurizing media for the apparatus illustrated in FIG. 2 is furnished by a canister 24 filled with a liquified gas such as CFC. While the use of CFC 12 is currently regulated by environmental (E.P.A.) regulations within the United States, it is noted that at the present time a combination of chlorofluorocarbon gases (CFC) may be used for this purpose. A good choice in the non-flammable 40%/60% blend of CFC 22/142a (a) "Genetron Propellants in Aerosol Products" publication no. TSD-0485 Allied Corp. (b) "A New Era in Aerosol Propellants" publication no. E-70287 DuPont, Inc. For these gases, a neoprene valve stem should be used in the aerosol can. The canister 24 is equipped with an inexpensive tilt action spring loaded aerosol discharge valve 25 such as that manufactured by Precision Valve of Yonkers, N.Y., which regulates the discharge of CFC from the canister. When the valve is depressed laterally or inwardly along the longitudinal axis of canister 24, CFC is discharged. When the valve is released, the discharge of CFC is terminated. The valve is spring-loaded to a normally closed position in a conventional manner.

Thus, the present invention is able to utilize low cost standard containers that have become popular in the spray dispenser art, particularly the cosmetic art.

When pressurization of the physiological bag is initialed as will be described later, the elastic sidewall 26 engages the extended arm 53, and urges it to the position 53a illustrated by dotted lines in FIG. 2. By engaging the extended arm 53 through the elastic wall 26, the spring-loaded discharge valve 25 is opened, and CFC gas begins to flow out of canister 24 and into the first pressure chamber 32. From chamber 32, the CFC flows through the openings 57 defined in one way valve means 19, as illustrated by arrow P, into chamber 58 and three way valve 34 through conduit 27a, to port 27 and the pressure chamber 33, surrounding bladder means 20. The pressure thus exerted by the bladder 20 is exerted on the side walls of the disposable bag of sterile physiological solution 23 to the desired level. A substantially uniform cross-sectional area is formed between bladder 20, and the sterile bag of physiological solution 23 to thereby ensure a relatively constant pressurization of the fluid to be discharged through conduit 23a. When the sealed chambers 32, 33 have been pressurized to a predetermined level, which may be 300 torr, the elastic wall 26 is expanded and no longer exerts an inward pressure on extended arm 53. The cross-sectional area of elastic diaphragm 26, the pressure/volume characteristics of the elastic material used, the predetermined pressure level, and the loading required on valve 25, to cause discharge CFC therefrom, are carefully balanced to provide a relatively even discharge of CFC from canister 24, each time the pressure in chamber 32 drops below 300 torr. As the sterile physiological solution is discharged through conduit 23a, the volume of bag 23 will decrease, thereby increasing the volume of chamber 33 defined between the bladder 20 and the sidewalls 13, 14. As this volume increases, the pressure existent in chambers 32, 33 will decline, thereby allowing the elastic wall 26 to collapse into engagement with extended arm 53, which will actuate the discharge valve 25 to admit additional CFC to the pressure chambers 32, 33.

When the sterile physiological solution has been discharged from the disposable bag 23, as may be observed through the sidewalls 13, 14, upper cap member 28 is normally depressed to flex the elastic sidewall 26 outwardly and out of engagement with the extended arm 53. A dump valve 35, such as a three way stop clock, is then rotated to allow the CFC in chambers 32, 33 to escape through port 35 to the outside atmosphere. The chamber is then unlatched by breaking off ball 38 to remove latch member 22 and then opening flap member 16, to allow the empty bag to be discarded, and, if desired, a new bag of sterile physiological solution to be inserted therein.

The forces involved in balancing the area of the elastic wall, the force loading of the elastic wall, and the discharge valve of the canister will be described with respect to FIGS. 6-8. While different types of discharge valves or elastic loadings for the wall or a diaphragm may alter the specifics of the calculations hereinafter provided, the general principles involved are applicable to all of the various embodiments.

In the present invention an elastic wall, diaphragm or balloon is used with a canister having a spring-loaded discharge valve. One such balloon is the latex balloon made by Shiley, Laboratories, Irvine, Calif., part no. BSVD-300. The elastic wall diaphragm or balloon is stressed along a force vector by manual actuation to overcome the spring-loaded discharge valve and cause the discharge of the CFC gas into the first pressure chamber. As the elastic wall, diaphragm or balloon is further stressed it expands away from the spring-loaded discharge valve, thereby establishing a predetermined pressure within the first pressure chamber. The first pressure chamber is in fluid communication with either the bag of physiological solution, or bladder 20 which directly engages the bag of physiological solution. The bladder 20 also provides an additional barrier to protect against an accidental gas embole which may occur if the bag of physiological solution has or develops a pin hole leak. As physiological solution is discharged, the pressure in chambers 32 and 33 declines. As the pressure declines, the elastic wall, diaphragm or balloon contracts along a force vector, thereby causing the actuation, directly or indirectly, of the spring-loaded discharge valve, and the subsequent release of CFC into the first pressure chamber to repressurize the first chamber to the predetermined level. Variations in predetermined pressure can be accomplished by variations in wall thickness, wall configuration and material.

FIGS. 3-5 illustrate an extremely simple version of the present invention. In this version, a canister of CFC or other compressed gas 224 is equipped with a spring-loaded discharge valve 225 and a trigger means 253 which interact with an inflatable balloon 226 having an end cap 251 and a discharge conduit 227. The conduit 227 may be connected to port 27 of the device as illustrated in FIGS. 1 and 2. The first chamber 233 is defined within the walls of balloon 226, and communicates through conduit 227 with an expandable bladder 20 which is in direct engagement with a bag of physiological solution 23 as illustrated in FIGS. 1 and 2.

As illustrated in FIG. 3, the device is collapsed with the balloon 226 folded about trigger means 253, and chamber 233 is at ambient atmospheric pressure. The end cap 251 is in position A illustrated in FIG. 3. When actuation of the device is desired, the conduit 227 coupled to expandable bladder 20 and the end cap 251 is raised to the position illustrated at arrow "B" in FIG. 4. As the balloon is raised, the sidewall of the balloon 226 engages the trigger 253, laterally deflecting the trigger, and actuating the spring-loaded valve 225 to cause the discharge of CFC from the pressurized canister 224. In response to the discharge of the pressurizing fluid, balloon 226 is inflated, and pressure flows through conduit 227 to the inflatable bladder 20 to pressurize the bag of physiological solution.

After reaching a predetermined pressure, the balloon 226 will expand away from the trigger means 253 thereby allowing spring-loaded valve 225 to return to its original position, cutting off the supply of additional CFC from canister 224. A predetermined pressure level is then maintained in chamber 223 until the discharge of physiological solution from bag 23 causes an expansion of the expandable bladder 20 and a reduction in pressure in the expandable bladder, conduit 227, and the first pressure chamber 233.

The resilient balloon 226 is clamped to the upper outer periphery of canister 224 as illustrated in 262 to define a pressure chamber 233 within the balloon.

As physiological solution is discharged from the bag 23, the pressure drop in the first pressure chamber 233 results in a contraction of balloon 226, until the sidewall of the balloon engages trigger means 253. When 253 is engaged, the contractive force of the balloon 226 overcomes the spring-loaded force of valve 225 thereby resulting in the additional discharge of CFC from the pressurized canister as illustrated in FIG. 4. The length of the arm can be adjusted to provide the desired mechanical advantage necessary to overcome the spring force of the aerosol valve. The trigger means 253 here and in the head of other figures has a large round smooth head to facilitate the necessary motion between it and the balloon membrane. Additionally, the head may be covered with a lubricating material such as silicone.

Figure 6:
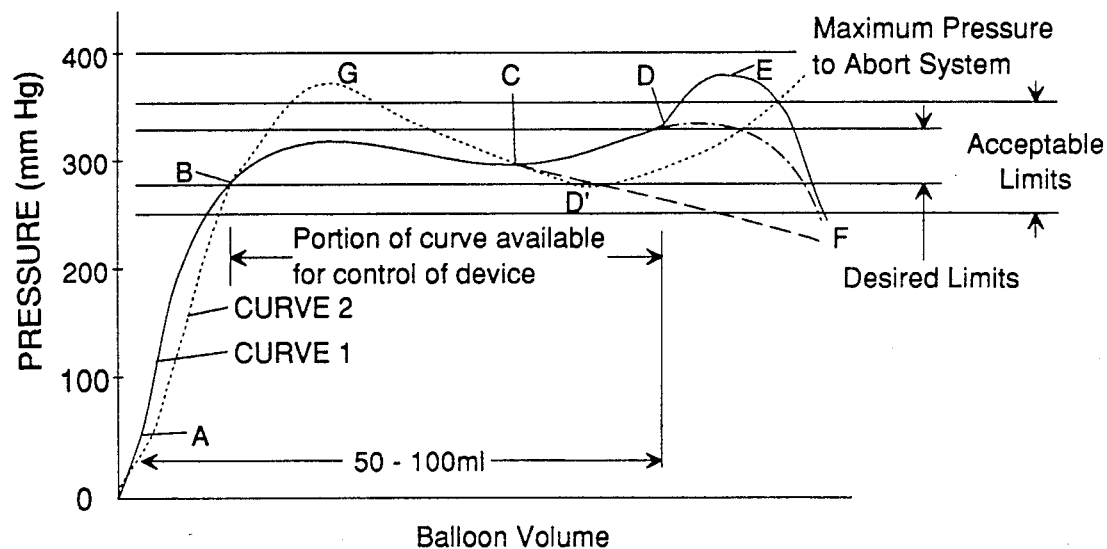
FIG. 6 is a graph which illustrates the desired pressure-volume characteristics of the preferred embodiments of the invention.

The desired pressure volume characteristics of balloon 226 are illustrated as curve 1 in FIG. 6, with balloon volume illustrated along the x axis, and pressure in mmHg illustrated along the y coordinate. Curve 1 from point A to point B illustrates the pressure required to achieve initial elastic deformation of the balloon wall. Once deformation is achieved, the curve slopes gradually upward as illustrated from point B to point C and covers the desired operational limits and the desired portion of the pressure/volume curve available for control of the device. The portion of the curve illustrated from point C to point F illustrated in dashed lines in FIG. 6 illustrates a characteristic common to elastic rubber devices wherein after a certain point, an increase in volume results in a decrease in pressure with no additional elastic force being generated. It is possible for the balloon to fall into uncontrolled expansion and deformation to the point of rupture if the pressure in chamber 223 passes point C, as illustrated in FIG. 6. For this reason, the present invention contemplates certain means that are used to alter the normal pressure/volume curve from point C as illustrated by the curve from point D to point E. To create this safety zone D-E, the balloon configuration is altered, or an external cage is used to change the ratio of surface area to balloon volume that expands as the balloon is pressurized. As illustrated in FIG. 6 the engagement of the cage (illustrated at 560 in FIGS. 11 and 12) begins to deform the curve, as illustrated from C to D. At point D, the balloon has fully engaged the cage, leaving only a small portion available for continued expansion. This causes an abrupt change in the pressure/volume curve, illustrated from D to E, until the balloon membrane herniates and the pressure declines, as noted at E to F.

Alternately the problem associated with uncontrolled expansion may be solved by using a synthetic elastic rather than natural latex. Curve 2, illustrated as a dotted line in FIG. 6, illustrates the pressure volume characteristics of an elastic wall formed of vulcanized synthetic polyisoprenes having a significant proportion, if not all, of their monomeric units joined with a CIS orientation. The use of this material in the present invention will be further described with respect to FIGS. 17-19.

Alternately, the one way valve 19 illustrated and described with respect to FIG. 1, may be used to prevent uncontrolled expansion of the elastic wall 26, as herein before described.

Further, the regulated pressure can be varied by altering the thickness, the balloon diameter, the ratio of the balloon length to diameter, and the composition or materials used in forming the balloon.

Figures 7, 8:
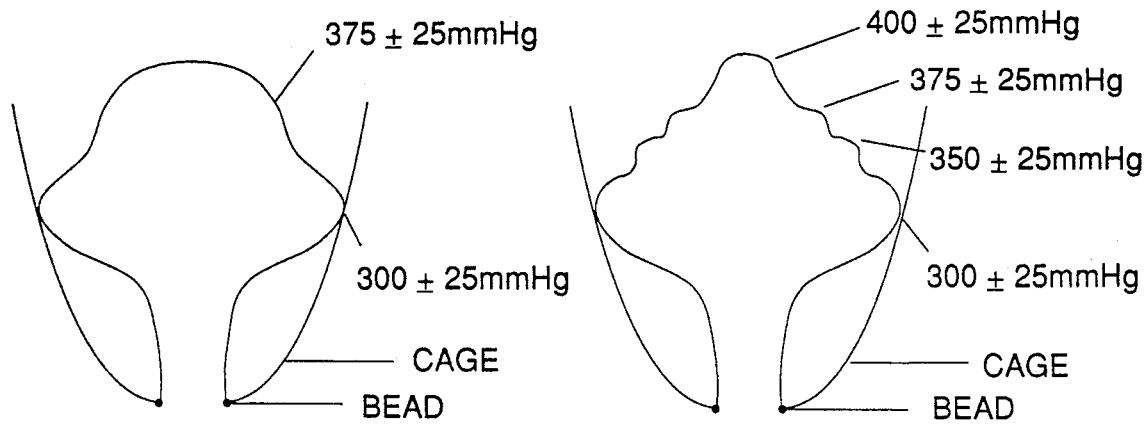
FIG. 7 is a diagrammatic illustration of one elastic wall configuration having differential pressure-volume characteristics.
FIG. 8 is a diagrammatic illustration of a second elastic wall configuration having multiple pressure-volume characteristics.

FIG. 7 illustrates a balloon having a configuration which provides for multiple pressure-volume characteristics. If a latex balloon is configured as illustrated in FIG. 7, the central large diameter portion will expand along the central flat portion of the curve from B to C illustrated in FIG. 6 at 300±25 mmHg. The upper portion of the balloon, being of smaller diameter, with a different perimeter to volume relationship, will expand at 375±25 mmHg. This additional change in pressure volume characteristics, in conjunction with the previously described cage, can be utilized in the present invention to provide the sharp rise between D and E in the pressure volume curve illustrated in FIG. 6.

FIG. 8 illustrates an embodiment of the invention in which a plurality of pressure/volume characteristics are provided by providing a series of gradually reducing diameters progressively arranged along the outer spherical surface of the balloon.

Figure 9:
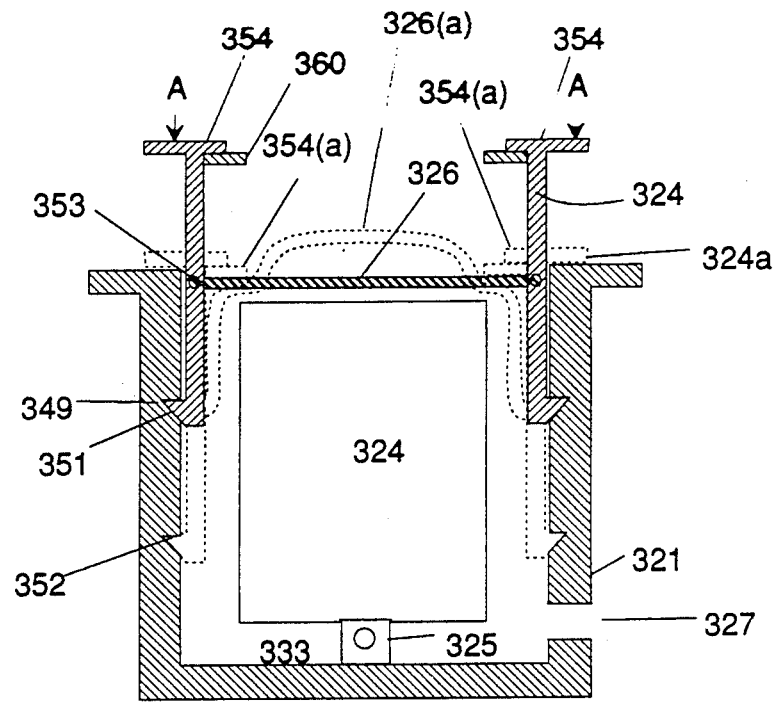
FIG. 9 is a diagrammatic illustration of an alternate version of the present invention.

FIG. 9 provides still another alternate arrangement of providing a selectable and variable sharp change in the pressure volume characteristics of the device at a desired pressure level. A housing member 321 defines a storage receptacle for a canister 324 of CFC having a spring-loaded discharge valve 325 mounted thereon. A discharge port 327 is in fluid communication with port 27 and the expansible bladder 20 previously illustrated in FIGS. 1 and 2. A reciprocating member 324 is slidably mounted within the walls of housing 321 having an engagement rib 349 defined on the lower portion thereof which engages either notch 351 or notch 352. Across the medial portion of reciprocating member 324 is stretched an elastic diaphragm 326 which is secured to the reciprocating member 324 by a bead and groove arrangement as illustrated at 353. When shipped, the device is assembled as illustrated in FIG. 9. When it is desired to actuate the device, and pressurize chamber 333 and the expandable bladder 20, the reciprocating member 324 is depressed downwardly as indicated by the arrow a in FIG. 9 to a lowermost position wherein the rib 349 will engage the lowermost groove 352. When the reciprocating member 324 is urged downwardly, the diaphragm 326 is stretched over the bottom of the aerosol canister 324 as illustrated by the dotted lines in FIG. 9. The pressure of this manual actuation overcomes the spring-loaded valve 325 and allows the contents of canister 324 to pressurize the pressure chamber 333 and eventually cause the expansion of diaphragm 326 to the position illustrated in 326(a). As the diaphragm expands upwardly, pressure on the canister 324 is relieved, and the spring-loaded valve 325 then closes at the predetermined and desired pressure level. Reciprocating member 324 is equipped with an inwardly extending rim 354 and interchangable disc 360 which engages the upwardly expanding elastic diaphragm 326 as illustrated at 354(a) to thereby change or alter the perimeter to volume relationship of the expanding wall. In this manner, the curve is suddenly altered as illustrated between points D and E in FIG. 6. By varying the inner diameter of the disc 360 one can selectively alter the pressure-volume characteristics of the device, and the predetermined pressure present within chamber 333. While the device illustrated in FIG. 9 is illustrated as a cylinder, it should be noted that the device would function equally well as a rectangle or other polygon.

Figure 10:
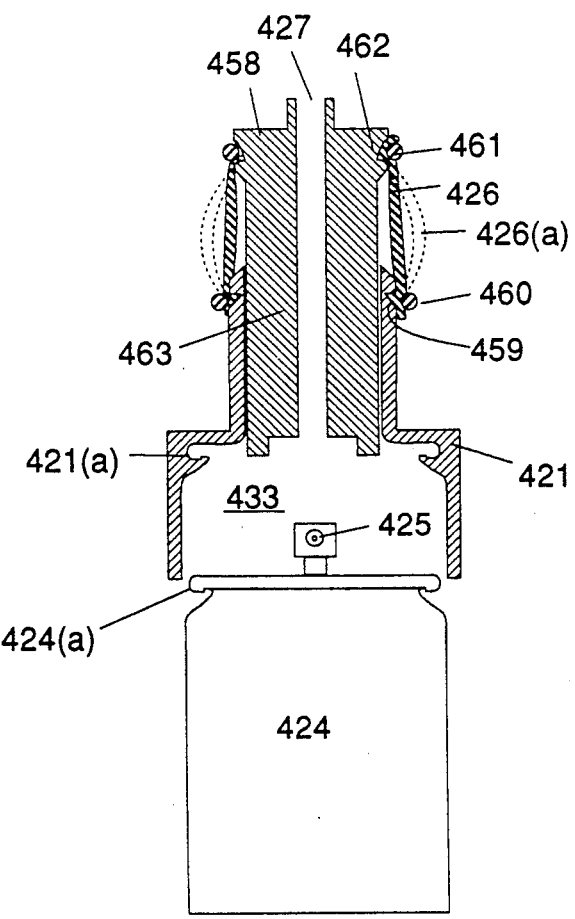
FIG. 10 is a diagrammatic and partially cross-sectioned illustration of another version of the present invention.

Another version of the second embodiment is illustrated in FIG. 10 wherein the canister of pressurized fluid 424 is equipped with a bead 424(a) and a spring-loaded discharge valve 425. The housing member 421 is equipped with a deformable tongue and groove indicated at 421(a) which is designed to snap around the bead 424(a) when it is desired to actuate the device. The orifice 427 is connected via tubing to port 27 and bladder 20 as illustrated in FIGS. 1 and 2. The device illustrated in FIG. 10 is equipped with a reciprocating valve engagement means 463 which is secured to housing means 421 by means of an elastic annular wall 426. The elastic annular wall is secured to housing 421 by means of groove 459 and clamp ring 460.

Likewise, the reciprocating member 463 is secured to the elastic annular wall 426 by means of groove 462 and clamp ring 461. The device is shipped in two separate pieces, and when it is desired to pressurize the expandable bladder 20, a tubing or conduit is first engaged at 427 to place chamber 433 in fluid communication with the expandable bladder 20. The housing member 421 is then urged downwardly into engagement with the canister 424 until the snap groove 421(a) has engaged bead 424(a). Alternately, the housing member 421 may be formed in two sliding ports as illustrated in FIG. 9, for actuation of this device. The length of reciprocating member 463, and the length of the annular elastic wall 426 are chosen so that the initial elastic deformation of wall 426 will overcome the spring resistance of discharge valve 425, resulting in the pressurization of chamber 433, and conduit 427. As chamber 433 is pressurized, the annular elastic wall 426 will be deformed outwardly as illustrated in FIG. 426(a) thereby raising the reciprocating member 463, and allowing the spring-loaded valve 425 to rise upwardly, and thereby shut-off the flow of further fluid from the pressurized canister 424. When the bag of physiological solution illustrated in FIGS. 1 and 2 has discharged sufficient fluid to increase the volume in the inflatable bladder 20, conduit 427, and first pressure chamber 433, the pressure therein will be reduced, and the elastic force generated by annular member 426 will overcome the spring-loaded pressure of valve 425 resulting in a subsequent repressurization of chamber 433, conduit 427, and bladder 20.

Figure 11:
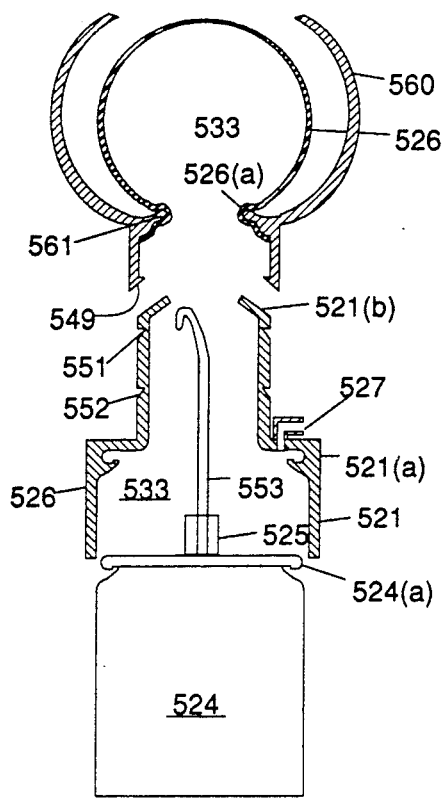
FIG. 11 is a diagrammatic and partially cross-sectioned illustration of another version of the present invention.

Another alternate version of the second embodiment is illustrated in FIG. 11 where the canister of pressurized fluid 524 is equipped with a spring-loaded discharge valve 525, and a trigger 553 as was previously described with respect to FIGS. 3-5. The balloon 526 is formed with a concentric groove 526(a) which engages a ridge 561 formed on the inner walls of cage member 560. Cage member 560 also has defined on its lowermost portion annular ridge 549 which is used to engage one of two grooves, 551 or 552 as illustrated in FIG. 21.

As illustrated in FIG. 11, the device can be shipped with the cage member 560 assembled to housing member 421, or in the alternative, housing member 521 can be shipped in engagement with canister 524, or the device may be shipped in three separate pieces. When it is desired to actuate the device, the housing member is snapped over canister 524 to provide that groove 521(a) engages the bead 524(a) defined on the extremity of canister 524. Cage member 560 is then slid downwardly as illustrated in FIG. 11 to move the engaging bead 549 from groove position 551 to groove position 552. In doing so, the upper portion 521(b) of housing member 521 will engage the lowermost surface of balloon 526 and seal the balloon against bead member 561. When the devices are snapped together in their final and actuated position, the balloon member 526 will engage trigger means 553, and cause deflection of the spring-loaded valve 525 which will result in the pressurization of the balloon and the first pressure chamber 533. The embodiment illustrated in FIG. 11 is then connected via discharge port 527 to the port 27 and bladder 20 as illustrated in FIGS. 1 and 2.

Figure 12:
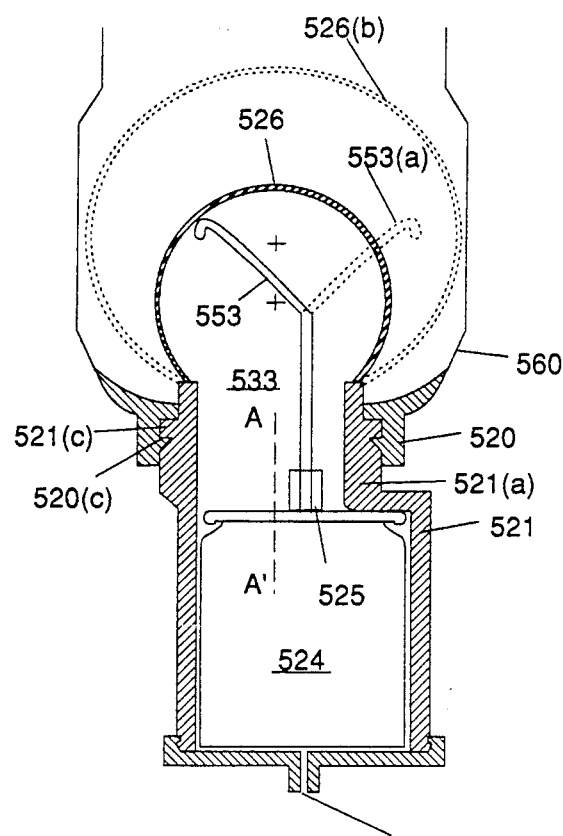
FIG. 12 is a diagrammatic and partially cross-sectioned illustration of another version of the present invention.

The device illustrated in FIG. 11 uses a reciprocal or sliding form of actuation, while the device illustrated in FIG. 12 illustrates a rotational or twist form of actuation. The device illustrated in FIG. 12 is essentially the same as the device illustrated in FIG. 11, except that housing member 521 defines thereon an off center circular member 521(a) with a rotating annular collar 520. Housing member 521(a) defines an annular bead 521(c) while rotating member 520 defines a mating annular groove 520(c). When the device is shipped, it is shipped as illustrated in FIG. 12 wherein the confines of annular balloon 526 exert no pressure on trigger means 553. When it is desired to actuate the device, the housing member 521 is rotated with respect to collar 520, which either rotates trigger 553 relative to canister 524 or also rotates canister 524 and trigger means 553 to the position illustrated in 553(a). Another technique is to have balloon 526 pretwisted 180°. This method eliminates the requirement for a sliding seal between 520 and 521. When rotated, the balloon member 426 engages trigger means 553, and causes deformation of the spring-loaded valve 525, and the pressurization of chamber 533 in a manner similar to previously described with respect to FIG. 11. The balloon 553 will then expand to the position illustrated in 526(b) in FIG. 12 thereby allowing trigger means 553(a) to return to its normal position closing the discharge valve 525. In this embodiment, the first pressure chamber 533 communicates through conduit 527 to port 27 and the bladder means 20 as previously described with respect to FIGS. 1 and 2.

In both FIGS. 11 and 12, the cage members 560 serve as a means to alter the pressure volume characteristics of balloon means 526. As the balloon expands into contact with cage member 560, the pressure/volume relationship is changed, thereby providing the curve between points C and E illustrated in FIG. 6.

Figure 13:
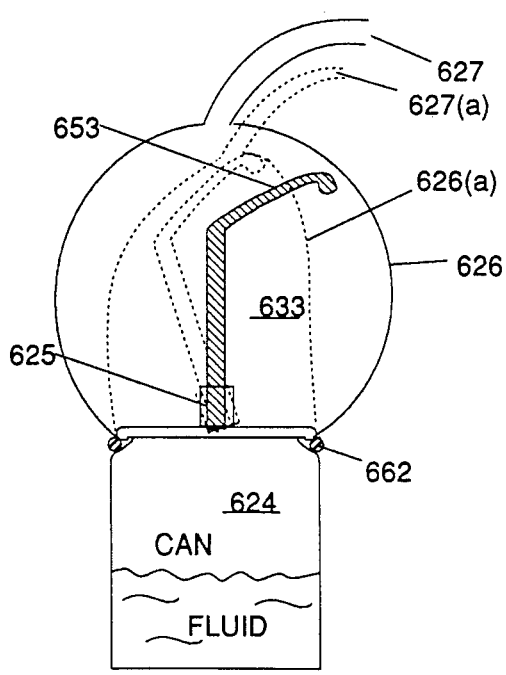
FIG. 13 is a diagrammatic and partially cross-sectioned illustration of still another version of the present invention.
Figure 14:
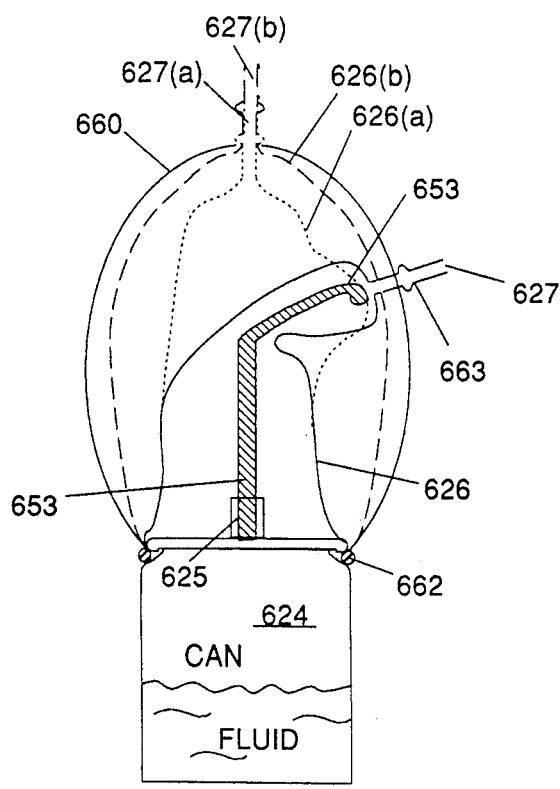
FIG. 14 is a diagrammatic and partially cross-sectioned illustration of still another version of the present invention.

Still another version of the invention is illustrated in FIGS. 13 and 14, with FIG. 13 illustrating a simple version, and FIG. 14 illustrating a more complex version equipped with a means for altering the pressure volume characteristic of balloon 626. As illustrated in FIG. 13, the expansible balloon 626 is formed with a pigtail conduit 627 which is connected to the port 27 and bladder 20 as previously described with respect to FIGS. 1 and 2. The balloon member 626 is secured with the canister 624 by means of a groove and clamp ring 662 as illustrated in FIG. 13. When it is desired to actuate the device, the pigtail conduit 627 is pulled upwardly engaging trigger means 653 and opening discharge valve 625 in a manner as previously indicated. As illustrated in FIG. 13, 626(a) illustrates the balloon in a contracted configuration, while 626 illustrates the balloon in an expanded configuration. As indicated previously with respect to the other embodiments, as the physiological solution is discharged from bag 23, the volume in the expandable chamber 20 expands, thereby lowering the pressure in conduit 623 and the first pressure chamber 633. This reduction in pressure results in a contraction of the balloon member 626 which engages the trigger means 653 to actuate valve means 625 and thereby repressurize the first pressure chambers 633.

In the embodiment illustrated in FIG. 14, the device illustrated in FIG. 13 is further equipped with a cage 660, having a partial circumferential groove 661 defined therein. The pigtail conduit 627 having a retaining means 663 is secured in the lowermost portion of slit 661 with the balloon means 626 folded in the manner illustrated in FIG. 14 about trigger means 653. When it is desired to actuate the device, the pigtail conduit 627 is moved upwardly to the position illustrated at 627(a) through the balloon configuration to the shape illustrated in FIG. 626(a). This results in an elastic deformation of the balloon along a force vector which acts on trigger means 653 to actuate the spring-loaded discharge valve 625. As the valve is actuated, the balloon member is expanded to the configuration illustrated at 626(b) thereby relieving pressure on the trigger means 653, and allowing the spring-loaded pressure valve 625 to close. When the balloon member 626 contracts due to a discharge in the physiological solution bag 23, it will re-engage the trigger means 653, resulting in a discharge of fluid through valve 625 to repressurize the apparatus.

Figure 15:
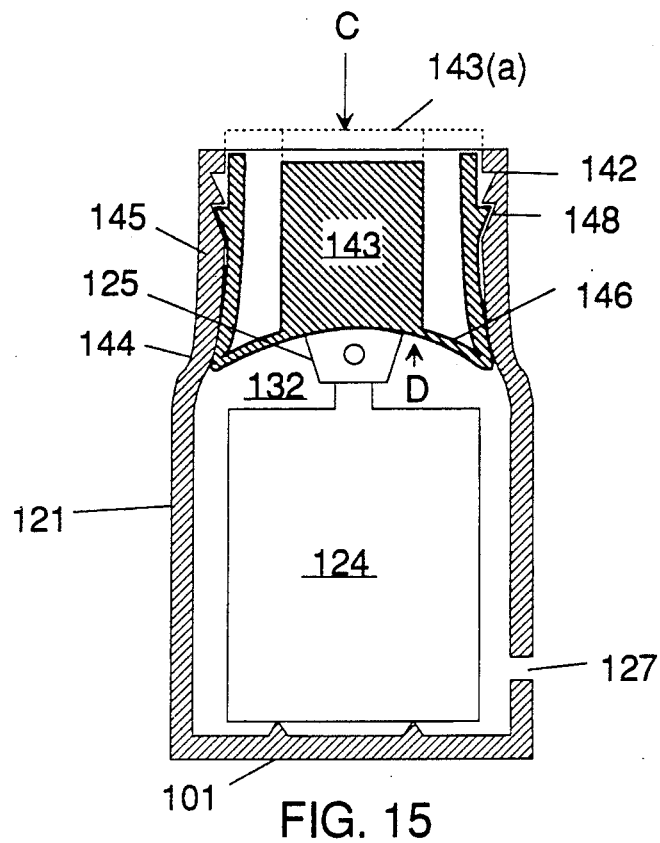
FIG. 15 is a partially cross-sectioned illustration of an alternate embodiment of the present invention, having a force loaded diaphragm suitable for use as a pressure regulating mechanism, illustrating first and second stages of operation.

In FIG. 15, a second embodiment of the invention is illustrated in cross-section, wherein the first pressure chamber 132 receives a canister of pressurized fluid 124, such as CFC or the like, having a reciprocal discharge valve 125 mounted thereon. The housing member 121 is formed with port 127 providing fluid communication between the first pressure chamber 132 and the port 27 of the sealable container shown in FIGS. 1 and 2.

The upper portion of housing 121 defines an annular groove 142 around its inner periphery, above the canister of pressurized fluid. A deformable force loaded diaphragm means 143 is illustrated in cross-section. Member 143 combines the function of the actuating mechanism and the elastic balloon 126. When shipped, member 143 is shipped in the position illustrated by the dotted line 143(a) with the annular ridge 145 engaging the annular groove 142. When it is desired to actuate the device, the member 143 is pressed downwardly into the direction of arrow C, moving the annular ridge 145 within the groove 148. Ridge 145, and groove 148 secure the force loaded diaphragm means 143 in the position illustrated in FIG. 15. This will result in the discharge of CFC from canister 124 through valve means 125. As the pressure builds in first pressure chamber 132, the diaphragm portion 146 will be displaced upwardly in the direction of arrow D, thereby allowing the discharge valve 125 to close, and preventing any further discharge of CFC from the container 124. In this embodiment, the pressure regulation is provided by matching the resilience and force generated by the deformation of the diaphragm portion 146, the force needed to actuate reciprocal valve 125, and the effective area of the diaphragm portion 146 of the resilient member 143.

Figure 16:
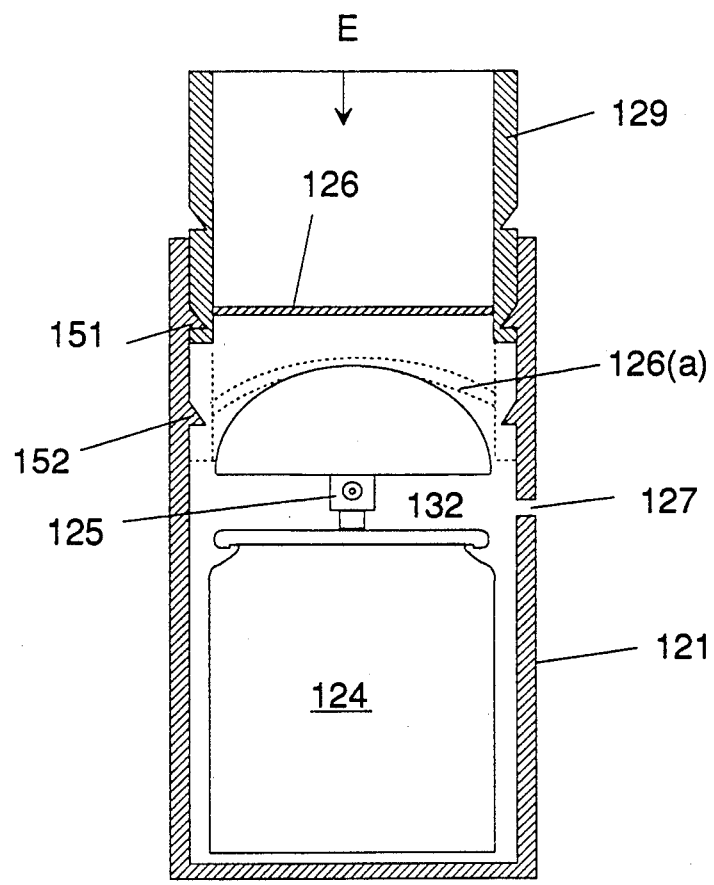
FIG. 16 is a partially cross-sectioned view of an alternate embodiment of the present invention, having a force loaded diaphragm suitable for use as a pressure regulating mechanism, illustrating first and second stages of operation of said diaphragm.

In FIG. 16, another version of the present invention is illustrated which is adapted to be used with a canister 124 of liquified gas, and a standard reciprocal discharge valve 125. In the embodiment illustrated in FIG. 14, a housing member 121 is adapted to receive the canister of pressurized fluid 124 and communicates with bladder 20 in the sealable container through a conduit or port 127. The discharge valve 125 is fitted with a semispherical member 104 which cooperates with the diaphragm means 126 to form a combined diaphragm and spring for functioning the constant pressure pump. In this embodiment, the elastic deformation of diaphragm 126 about the semispherical member 124 provides the force loaded component of the constant pressure pump.

Before actuation, the pump is stored in the position illustrated in FIG. 16 with the actuating mechanism 129 in its raised position. When it is desired to actuate the mechanism and pressurize the sealable container, the actuating mechanism 129 is displaced downwardly in the direction of arrow E until the groove 151 engages the latching ridge 152 formed on the inner side walls of housing 121. As the actuating mechanism 129 is displaced downwardly, the resilient and stretchable diaphragm 126 is stretched across the top of cap 104 as indicated by the dotted line 126(a) in FIG. 16. The elastic resilience of diaphragm 126 provides the force loading for the constant pressure pump. This initial actuation overcomes the resilient force present within the discharge valve 125, and permits the discharge of CFC into the first pressure chamber 132, port or conduit 127, and the sealable container (not shown in FIG. 16). As the pressure in the first pressure chamber 132 builds, the cap 104 and the diaphragm 126 are displaced upwardly opposite of the direction of arrow E by virtue of the pressure therein and the lower atmospheric pressure found on the opposite side of the diaphragm 126. When the pressure in the first pressure chamber 132 reaches the predetermined desired pressure, the diaphragm 126 has been stretched upwardly, which permits the discharge valve 125 to close, thereby preventing the escape of any CFC from canister 124. As a physiological solution is displaced from the sealable container, the pressure in the container, and the first pressure chamber 132 will drop, thereby enabling the resilient nature of diaphragm 126 to again open the discharge valve 125 to repressurize the first pressure chamber 132, and continue the discharge of the physiological solution at a constant pressure.

In the embodiment illustrated in FIG. 17 an infusion cuff is formed with, a double wall bag having an outer enclosure member 711 and an inner pressuring bladder 720 which are adapted to receive a disposable bag of physiological solution which is inserted through opening 707. The enclosure means and bladder are closed after the insertion of the bag of physiological solution by inserting one way fastening means 738 through opening 722 as illustrated in FIG. 18, and clinching strips 716 and 717 together. Strips 716 and 717 may be formed with a single block of plastic, or as illustrated in FIGS. 17 and 20, may be formed of strips of plastic 716, 716(a), 717, and 717(a). In the embodiment illustrated in FIGS. 17 and 20, strips 717, 717(a) and 716(a) are cut away in the center portion thereof to define an opening 709 which receives a dispensing conduit 23(a) attached to the disposable bag of physiological solution for discharge of the solution from the infusion device. One way closure means 738 includes a barbed member 739 which swings outwardly after passing through opening 722 to prevent the strips from being pulled apart. If a multiple use device is desired, the barbed member 739 can be folded back into recess 738(a) to permit withdrawal of the barb through opening 722. Alternately, as illustrated in FIG. 20, if it is desired to limit the infusion device to a single bag, closure members 740 may be equipped with double barbs which effectively prevent the user from re-opening the enclosure means and attempting to reuse the device.

Alternately, the opening 707 may be closed by a draw string 708 as illustrated in FIG. 19. In this embodiment, the heat sealed portion 706 defines the lower extremities of the pressurizing chamber, 733, and also defines the draw string cavity 705. In operation, the disposable bag of physiological solution is inserted through opening 707, and the draw string 708 pulled to close the opening and the drawstring is then secured with a temporary fastener. The somewhat loose fit of a draw string closure enables the egress of the dispensing conduit from the enclosure means 711.

If the infusion device is designed as a reusable device, the bladder 720 may be inverted to the position illustrated at 720(a) in FIG. 17, to assist in the removal of the spent bag of physiological solution.

The enclosure means 711 and the bladder 720 define therebetween a pressurizing chamber 733 which serves to exert a constant pressure on bladder 720, and thereby a constant pressure on the bag of physiological solution.

The invention as illustrated in FIG. 17 also includes a first pressure chamber 732 which is formed of a pair of cylindrical housing means 721 and 731 which are coupled by means of elastic wall member 726. Mounted within the first pressure chamber is a canister of pressurized fluid 724 which is equipped with a springloaded discharge valve 725 which discharges the pressurized fluid from canister 724 when depressed.

Upper cylindrical member 731 also includes a pair of integrally molded latch means 750, 751. The latch member 750, 751 engage opposing sides of piston member 752 which is used to actuate the device illustrated in FIG. 17 to 19. Piston 752 includes a plurality of detents or notches, such as those illustrated at 753, 754 which position piston 752 along a reciprocal path parallel to and coaxial with the reciprocal path of springloaded discharge valve 725.

The device is shipped in the state illustrated in FIG. 17, with the piston means 752 fully withdrawn, and the latches 750 and 751 engaging the lowermost notches or detents 753, 754. Ports 735 and 735(a) vent the first pressure chamber 732 to the ambient atmosphere. Likewise, pressurizing chamber 733 is vented to ambient atmosphere through port 727, first pressure chamber 732, and atmospheric port 735.

Alternately, piston member 752 and the upper portion of the upper cylindrical housing 731 may be equipped with a twist lock wherein the piston 752 may be rotated half a turn, depressed at any desired notch level, and then rotated back to lock the piston at the desired reciprocal position.

The first pressure chamber, including the cylindrical member 721 and elastic wall member 726 are joined together by means of band 742 which also secures enclosure means 711 to the first cylindrical housing 721. Band 742 may also be formed of an elastic material which also serves as a safety mechanism, which in the event of over pressurization, will allow separation between the infusing bag and the pressure source. Alternately, enclosure means 711 may be heat sealed to the first cylindrical means 721, and the elastic wall means 726 secured thereto by means of a snap ring as illustrated by snap ring 755 which secures elastic wall 726 to the upper cylindrical housing 731. Alternately, the elastic wall means 726 may be secured to upper and lower housing members 721, 731 by an adhesive.

Housing member 711 and bladder member 720 may be formed of a thin walled plastic as previously described with respect to FIGS. 1 and 2 wherein the thin wall (0.002 to 0.010 in.) is a polyethylene, nylon polyester, or polyester-polyethylene laminate. This provides a soft readily conformable bladder which will surround the bag of physiological solution and exert an even pressure throughout. Alternately the housing member 711 may be formed of a heavier gauge plastic with bladder 720 formed of a thin wall laminate. The use of polyethylene enables the use of heat sealing techniques to form the bag, while the use of a nylon or polyester-polyethylene laminate enables the thickness of the wall to be reduced, while still retaining the heat seal capability of the polyethylene.

In operation, the disposable bag of physiological solution is first inserted into cavity 704 and the open end 707 closed by means of either one way closure means 716, 717 or the draw string 708. Actuation of the pressure regulating means is achieved by depressing latch members 750, 751 inwardly as illustrated by the arrows A, A' in FIG. 17. Simultaneously, piston member 752 is reciprocated downwardly as illustrated by the arrow B in FIG. 18. This enables the pauls of latch means 750, 751 to be moved upwardly to detents 760, 761. As piston member 752 reciprocates downwardly within cylindrical housing 731, the o-ring 755 seals ports 735, 735(a) thereby closing communication between atmosphere and the first pressure chamber 732. As the piston member 752 is reciprocated downwardly, the spring discharge valve 725 on the canister pressurized fluid 724 is first opened, and after the valve has reached its limit of travel, the elastic wall 726 is stretched upwardly to generate a linear force coaxial with and surrounding canister 724. The linear force generated by elastic wall means 726 is a contractive force vector which thereby maintains springloaded discharge valve 725 in its open position, releasing the pressurizing fluid from canister 724. The pressurizing fluid then flows from chamber 732, through port 727, to the pressurizing chamber 733 to collapse the bladder means 720 around the bag of physiological solution, and thereby pressurize the solution within the bag.

As the pressure in the first pressure chamber 732 continues to build, elastic wall 726 begins to expand outwardly and upwardly as illustrated in FIG. 19. At a predetermined pressure level, the piston 752 and the upper housing member 731 have been expanded upwardly a desired distance to allow springloaded discharge valve 725 to close, thereby pressurizing the first pressure chamber 732 and the pressurizing chamber 733 at the desired operating pressure. It should be noted that this pressure can be altered by the selective placement of latches 750, 751 in the series of notches or detents formed on piston 752. Depending upon the characteristics of the latex used for the elastic wall 726, different notches will result in different levels of predetermined pressure. The following description assumes the pressure volume curve 2 of FIG. 6. The first notch 753 is used as a shipping position and prevents the inadvertent actuation of the springloaded discharge valve 725 inasmuch as the lowermost ledge of the upper cylindrical member 731 abuts and rests on the uppermost portion of the lower cylindrical member 721 as illustrated in FIG. 17. Depressing the piston to the second notch 762 will result in a medium level predetermined pressure within the pressurizing chamber 733 and the first pressure chamber 732. This is because of the upwardly rising portion of the initial portion of the pressure volume curve illustrated at point B in FIG. 6. Depressing the piston to the next notch 761, will result in the highest predetermined pressure as the point of deformation travels along the pressure volume characteristic curve to point G, as illustrated in FIG. 6. Depressing the piston to the third notch 763 will result in a second medium predetermined pressure, as the pressure volume characteristic curve reaches point C of curve 2 illustrated in FIG. 6. Finally, setting the detents 750, 751 in notch 764 will result in the lowest pressure, as the curve drops downwardly to point D' of curve 2, illustrated in FIG. 6.

It should be noted that the device illustrated in FIG. 17-19a provides a pressure regulator, a pressure indicator, and an over pressure relief mechanism, all of which are connected to the pressurizing chamber 733 through a single port 727. Piston member 752, and the upper cylindrical housing 731, together with a springloaded discharge valve 725 provide a means that is responsive to the movement of the elastic wall 726 to selectively open the discharge valve 725, and thereby pressurize the first pressure chamber 732. As illustrated in FIG. 19a, when fluid is discharged from the bag of physiological fluid, the volume enclosed within bladder 720 will decrease, increasing volume 733 and lowering the fluid pressure in the pressurizing chamber 733. This lowered pressure in chamber 33 will then cause a transfer of fluid from first chamber 732 thereby causing the contraction of volume 732 and of elastic wall 726 which will again bring piston 752 into engagement with canister 724, opening the springloaded discharge valve 725. As discharge valve 725 is opened, additional pressurizing fluid will flow from the canister 724, thereby raising the pressure, and increasing the volume in first pressure chamber 732. As the volume of chamber 732 as illustrated in FIG. 19 is increased, piston 752 is lifted upwardly, allowing springloaded discharge valve 725 to close at the desired predetermined pressure.

The elastic wall 726 provides not only a predetermined pressure regulating function for the infusion device, but also provides a pressure indicator which is visible by means of the outwardly bowing walls, illustrated in FIG. 19. In addition, a runaway pressure condition resulting from the failure of the springloaded valve 725 will result in the gross distention and/or rupture of elastic wall 726, thereby preventing possible injury to the patient by virtue of over pressurization of the infusion fluid. Over expansion of elastic wall 726 will also cause said wall to thin out at its points of attachment indicated at 742 and 755. As elastic wall 726 thins out from distention, it reaches a thickness value that allows its escape from between clamp 755 and wall 731, again protecting against overpressurization.

I claim:

1. A constant pressure infusion device for dispensing a physiological solution from a sterile disposable bag, said device comprising:
   (a) a housing member, said housing member having:
      (i) non-expandable walls, said walls arranged to receive a disposable bag of physiological solution therewithin, said bag having a dispensing conduit extending therefrom for discharging physiological solution therethrough;
      (ii) an inflatable means for pressurizing said bag of physiological solution within said walls,
   (b) a first pressure chamber, said chamber configured to receive a canister of pressurized fluid having a spring-loaded discharge valve mounted on said canister, said first pressure chamber being in fluid communication with the inflatable means,
   (c) at least one elastic wall defined by said first pressure chamber, said elastic wall, when stressed, generating at least one contractive force vector,
   (d) means for engaging said spring-loaded discharge valve along one of said contractive force vectors to selectively open said spring-loaded discharge valve to pressurized the first pressure chamber to a predetermined constant pressure.

2. A constant pressure infusion device for dispensing a physiological solution from a sterile disposable bag, said device comprising:
   (a) a flexible, non-expandable housing member, said housing having first and second sidewalls joined together along three adjoining seams to form an open pouch, said pouch having an open end with one of said sidewalls being extended to form a closure flap for closing the open end of said pouch,
   (b) a flexible bladder means for receiving said bag of physiological solution therewithin, said bladder means disposed within said housing and sealed to said housing along the open end of said pouch,
   (c) closure means for securing said closure flap to the exterior of the opposing coplanar wall to thereby secure said bag of physiological solution within said bladder and said housing, said closure means defining an opening therein for a dispensing conduit extending from said bag of physiological solution,
   (d) inlet means for pressurizing a chamber formed between said housing member and said bladder, said chamber extending over substantially the entire area of said bladder when said disposable bag of physiological solution is inserted therein,
   (e) constant pressure means for supplying a predetermined fluid pressure to said chamber.

3. A constant pressure infusion device as claimed in claim 2 wherein said housing is formed of coplanar transparent plastic wall members which are heat sealed at said three adjoining seams.

4. A constant pressure infusion device as claimed in claim 2, wherein said closure means includes a plurality of one way fastening means arranged in serial order on the outer portion of said sidewall, said fastening means enabling a predetermined number of closures.

5. A constant pressure infusion device as claimed in claim 2, wherein said constant pressure means includes a disposable canister of pressurized fluid, said canister having a springloaded discharge valve and being in fluid communication with said inlet means.

6. A constant pressure infusion device as claimed in claim 2, wherein said constant pressure means includes an elastic wall surrounding said springloaded discharge valve, said elastic wall, when stressed generating at least one contractive force vector, and means responsive to said contractive force vector to actuate said discharge valve.

7. A constant pressure infusion device as claimed in claim 2, which further includes a first pressure chamber defined at least in part by said elastic wall, said first pressure chamber being in fluid communication with said chamber formed between said housing member and said bladder by means of a one way valve.

8. A constant pressure infusion device for dispensing a physiological solution from a sterile disposable bag, said device comprising:
   (a) an enclosure means, said enclosure means defining a pressurizing chamber for receiving a disposable bag of physiological solution therewithin, said bag having a dispensing conduit extending therefrom for discharging physiological solution therethrough;
   (b) a first pressure chamber, said first chamber adapted to receive a canister of pressurized fluid having a discharge valve mounted on said canister, said first pressure chamber being in fluid communication with said pressurizing chamber;
   (c) a deformable and elastic wall member surrounding a portion of said first pressure chamber and in fluid communication therewith, said elastic wall arranged to generate a first force vector until the fluid pressure in said first chamber reaches a predetermined level;
   (d) means responsive to the movement of said elastic wall member along said force vector to selectively open said discharge valve to pressurize the first pressure chamber to said predetermined constant pressure;
   whereby the elastic wall member will selectively actuate the discharge valve to admit pressurized fluid into said first pressure chamber in response to a drop of pressure therein, said drop resulting from the discharge of physiological solution from disposable bag.

9. A constant pressure infusion device as claimed in claim 8, wherein said enclosure means further comprises an inflatable infusion cuff.

10. A constant pressure infusion device as claimed in claim 9 wherein said infusion cuff further defines a pouch for receiving said disposable bag, said pouch being open along one side thereof for receipt of said disposable bag.

11. A constant pressure infusion device as claimed in claim 10 wherein said infusion cuff further includes closure means for closing said pouch along said open side after the insertion of said disposable bag.

12. A constant pressure infusion device as claimed in claim 11 wherein said closure means for closing said pouch includes a plurality of one way fasteners.

13. A constant pressure infusion device as claimed in claimed 10 wherein said closure means for closing said pouch includes a drawstring.

14. A constant pressure infusion device as claimed in claim 10 wherein an inner wall of said pouch may be inverted for assistance in the removal of said disposable bag.

15. A constant pressure infusion device as claimed in claim 9 wherein said inflatable infusion cuff is formed of a heat sealed plastic film which completely encloses said disposable bag.

16. A constant pressure infusion device as claimed in claim 15 in which said plastic film is a substantially transparent polyester-polyethylene laminate.

17. A constant pressure infusion device as claimed in claim 8 wherein said first pressure chamber includes first and second cylindrical walls which are joined by said elastic wall member.

18. A constant pressure infusion device as claimed in claim 17 wherein said first pressure chamber includes a piston mounted in fluid sealing engagement with said first cylindrical wall to close the end thereof, said piston being moveable between at least a first open position and a second closed position in engagement with said canister of pressure fluid.

19. A constant pressure infusion device as claimed in claim 18 wherein said pressure chamber defines latch means for securing said piston in at least said first and second positions.

20. A constant pressure infusion device as claimed in claim 18 wherein said first cylindrical wall includes a vent opening to ambient atmosphere which is closed by said piston when said piston is moved to its second closed position.

21. A constant pressure infusion device as claimed in claim 18 wherein said piston is moveable to a plurality of closed positions to thereby selectively bias said elastic wall against said canister of pressurized fluid.

22. A constant pressure infusion device as claimed in claim 18 wherein said elastic wall provides pressure regulator, pressure indicator and over pressure relief functions.

23. A constant pressure infusion device as claimed by claim 22 wherein said pressure regulator, pressure indicator and over pressure relief provided with a single opening and connection to said pressurizing chamber.

* * * * *

UNITED STATES PATENT AND TRADEMARK OFFICE
CERTIFICATE OF CORRECTION

PATENT NO. : 5,013,303
DATED : May 7, 1991
INVENTOR(S) : Yehuda Tamari, et al.

It is certified that error appears in the above-identified patent and that said Letters Patent is hereby corrected as shown below:

Column 15, line 63: "pressuring" should read as --pressurizing--

Column 18, line 54: after "732" insert --as illustrated in FIG. 19--

Column 18, lines 54-55: delete "as illustrated in FIG. 19"

Column 19, lines 19-20, Claim 1: delete "mounted on said canister, and after "valve" insert --,with--

Signed and Sealed this

Ninth Day of March, 1993

Attest:

STEPHEN G. KUNIN

Attesting Officer

Acting Commissioner of Patents and Trademarks